(12) United States Patent
Astratov

(10) Patent No.: US 8,554,031 B2
(45) Date of Patent: Oct. 8, 2013

(54) FOCUSING MULTIMODAL OPTICAL MICROPROBE DEVICES

(75) Inventor: Vasily N. Astratov, Charlotte, NC (US)

(73) Assignee: University of North Carolina at Charlotte, Charlotte, NC (US)

( * ) Notice: Subject to any disclaimer, the term of this patent is extended or adjusted under 35 U.S.C. 154(b) by 190 days.

(21) Appl. No.: 13/321,965

(22) PCT Filed: Jun. 8, 2010

(86) PCT No.: PCT/US2010/037677
§ 371 (c)(1),
(2), (4) Date: Nov. 22, 2011

(87) PCT Pub. No.: WO2011/005397
PCT Pub. Date: Jan. 13, 2011

(65) Prior Publication Data
US 2012/0091369 A1    Apr. 19, 2012

Related U.S. Application Data

(60) Provisional application No. 61/187,690, filed on Jun. 17, 2009.

(51) Int. Cl.
*G02B 6/00* (2006.01)
*B01J 19/12* (2006.01)

(52) U.S. Cl.
USPC .......................................... 385/35; 250/492.1

(58) Field of Classification Search
USPC .............. 385/35–37, 122–129, 147; 250/227, 250/492.1
See application file for complete search history.

(56) References Cited

U.S. PATENT DOCUMENTS 4,720,642 A * 1/1988 Marks ........................... 307/150
4,740,048 A * 4/1988 Mori ............................... 385/25

(Continued)

OTHER PUBLICATIONS

Kapitonov A.M. et al:"Nanojet-induced modes in 1D chains of micropheres" Proceedings of the SPIE, SPIE, Bellingham, VA, US, US LNKD-DOI:10.1117/12.714486, vol. 6452, Jan. 1, 2007, pp. 645205-645211, XP007915219, ISSN: 0277-786X.

(Continued)

*Primary Examiner* — Akm Enayet Ullah
(74) *Attorney, Agent, or Firm* — Clements Bernard PLLC; Christopher L. Bernard; Lawrence A. Baratta, Jr.

(57) ABSTRACT

The present invention provides an optical microprobe device and method for focusing multimodal radiation with wavelength-scale spatial resolution and delivering the focused radiation to a specimen, including: a radiation source; and one or more of a plurality of optically transparent or semitransparent spheres and a plurality of optically transparent or semitransparent cylinders optically coupled to the radiation source; wherein the one or more of the plurality of optically transparent or semitransparent spheres and the plurality of optically transparent or semitransparent cylinders periodically focus radiation optically transmitted from the radiation source such that radiation ultimately transmitted to the specimen has predetermined characteristics. Preferably, the spheres or cylinders are assembled inside one of a hollow waveguide, a hollow-core photonic crystal fiber, a capillary tube, and integrated in a multimode fiber. Alternatively, the spheres or cylinders are assembled on a substrate. Optionally, the optical microprobe device also includes one or more of a waveguide, an optical fiber, a lens, and an optical structure disposed between the radiation source and the spheres or cylinders. Optionally, the spheres or cylinders are made from optically nonlinear or active materials that permit efficient nonlinear frequency generation and low-threshold lasing using the optical microprobe device.

27 Claims, 8 Drawing Sheets

(56) References Cited

U.S. PATENT DOCUMENTS

2005/0224335 A1* 10/2005 Carmignani et al. .... 204/157.15
2006/0000984 A1* 1/2006 Wolleschensky et al. . 250/458.1

OTHER PUBLICATIONS

Yang Seungmoo et al: "Photonic nanojet-induced modes in chains of size-disordered microspheres with an attenuation of only 0.08dB per sphere", Applied Physics Letters, AIP, American Institute of Physics, Melville, NY, US, US LNKD-DOI:101063/1.2954013, vol. 92, No. 26, Jul. 2, 2008, pp. 261111-261111, XP012107756, ISSN: 0003-6951.

Sykes, Charles H. et al: "Encapsulated microsphere arrays for applications in photonic circuits", Information Photonics, 2005. IP2005. OSA Topical Meeting on, IEEE, Piscataway, NJ, US, Jun. 6, 2005, XP031626987, ISBN: 978-1-4244-6637-5.

Astratov, Vasily N. et al: "Integrated Circuits of Coupled Microspheres for Optoelectronics Applications", Transparent Optical Networks, 2006 International Conference on, IEEE, PI, Jun. 1, 2006, pp. 77-81, XP031018016, ISBN: 978-1-4244-0235-9.

Astratov, V. et al: "Optical coupling and transport phenomena in chains of spherical dielectric microresonators with size disorder", Applied Physics Letters, AIP, American Institute of Physics, Mellville, NY, US, LNKD-DOI:10.1063/1.1832737, vol. 85, No. 23, Jan. 1, 2004, pp. 5508-5510, XP012063682, ISSN: 0003-6951.

Astratov, Vasily N., et al: "Optical Transport Phenomena in Coupled Spherical Cavities", Transparent Optical Networks, 2007, ICTON '07. 9th International Conference on, IEEE, PI, Jul. 1, 2007, pp. 65-70, XP031130606, ISBN: 978-1-4244-1248-8.

Chen, Z., et al.: "Highly Efficient Optical Coupling and Transport Phenomena in Chains of Dielectric Microspheres", Optics Letters, OSA, Optical Society of America, Washington, SC. US LNKD-DOI: 10.1364/OL.31000389, vol. 31, No. 3, Feb. 1, 2006, pp. 389-391, XP001238995, ISSN: 0146-9592.

Moeller, Bjorn N., et al: "Bloch modes and disorder phenomena in coupled resonator chains", Physical Review.B, vol. 75, 245327 Jun. 26, 2007, pp. 245327-1-245327-9, XP7915287 The American Physical Society DOI: 10.1103/PhysRevB.75.245327.

Kapitonov, A.A., et al: "Observation of Nanojet-Induced Modes with Small Propagation Losses in Chains of Coupled Shperical Cavities", Optics Letters, OSA, Optical Society of America, Washington, SC, US LNKD-DOI: 10.1364/OL.32.000409, vol. 32, No. 4, Feb. 15, 2007, pp. 409-411, XP001504487, ISSN: 0146-9542.

* cited by examiner

FOCUSING MULTIMODAL OPTICAL MICROPROBE DEVICES

CROSS-REFERENCE TO RELATED APPLICATION

The present non-provisional patent application/patent claims the benefit of priority of U.S. Provisional Patent Application No. 61/187,690, filed on Jun. 17, 2009, and entitled "OPTICAL MICROPROBE WITH SUBWAVELENGTH RESOLUTION," the contents of which are incorporated in full by reference herein.

STATEMENT REGARDING FEDERALLY SPONSORED RESEARCH OR DEVELOPMENT

The U.S. Government has a paid up license in the present invention and the right, in limited circumstances, to require the patent application/patent owner to license to others on reasonable terms as provided for by the terms of Award No. ARO W911NF-09-1-0450 awarded by the Army Research Office and Award No. ECCS-0824067 awarded by the National Science Foundation.

FIELD OF THE INVENTION

The present invention relates generally to optical microprobe devices and methods with wavelength-scale spatial resolution that are capable of using multimodal optical delivery systems, such as hollow waveguides, multimodal optical fibers, and the like. More specifically, the present invention relates to optical microprobe devices and methods that utilize a plurality of transparent or semitransparent small scale spheres, cylinders, or the like to create a compact focused beam of light, referred to as a "photonic nanojet." These optical microprobe devices and methods find applicability in material and biomedical modification and cutting applications, material analysis applications, data storage applications, and the like.

BACKGROUND OF THE INVENTION

Optical microprobe devices and methods are utilized in various photonic and biomedical applications where it is desirable to locally deliver the optical power from lasers, other radiation sources, and the like to small areas of modified or examined samples. For example, it may be desirable to cut or otherwise modify biological tissue or other material using light; collect reflected, scattered, or emitted light from a sample; encode data to/decode data from a material using light; etc. In such applications, the spatial resolution of the optical microprobe devices and methods is governed by the diameter of the focused light beam in a medium or sample under study—a key parameter. Typically, the spatial resolution of optical devices operating in far field is determined by the wavelength of the light utilized and the aperture of the objective-lens system, i.e. the diffraction limit. The efficient delivery of optical power is another key parameter, with greater optical power typically being desirable. The task of development of compact light-focusing tools for photonics and biomedical applications is challenging due to the multimodal structure of the beams propagating in the often flexible delivery systems of such devices. The potential applications of such technologies are endless, including nanoscale patterning, the formation of tiny holes in thin films, ultra-precise laser tissue surgery, the piercing of a cell, the spectroscopic characterization of individual particles, and the like.

Conventional optical microprobe devices and methods suffer from a number of significant shortcomings. Existing near-field optical microprobes have high resolution, but extremely limited optical transmission. Utilizing tapered optical fibers coated with opaque metallic films and tiny transmissive apertures, smaller spot sizes are obtainable, i.e. less than $\lambda$ (10-20 nm, for example). However, these optical microprobes typically fail to deliver adequate optical power. Existing far-field optical microprobes have high optical transmission properties, but very limited spatial resolution, especially in the case of multimodal input beams. Utilizing solid immersion lenses (SILs) or the like and perfectly collimated or conical beams of light, smaller spot sizes are also obtainable, i.e. less than $\lambda$ ($\lambda/2$, for example). However, such perfectly conical beams of light are not readily available in conventional optical delivery systems used in laser-tissue surgery and other applications. Typically, obtaining such perfectly conical beams of light requires the use of single mode optical fibers as the means of optical delivery. It should be noted, however, that single mode optical fibers are not readily available in the mid-infrared range of the spectrum. They also have limited coupling efficiency with many practical radiation sources, and limited power transmission properties. Instead, using multimodal beams in such systems results in greatly diminished spatial resolution, well below the diffraction limit. In any event, such optical microprobes, and others, do not allow for direct contact with a sample, i.e. tissue contact in a biomedical application, due to high refractive indices (~1.33 or larger) of the later, leading to defocusing of the beam. It should be noted, however, that such a contact mode of operation may be desirable in some applications, such as ultra-precise laser-tissue surgery applications, etc. Other existing optical microprobes may obtain better spatial resolution than the diffraction limit in an imaging mode, but require special spectral characteristics and material properties, such as fluorescence, nonlinearity, etc. These optical microprobes also typically fail to deliver adequate optical power. Further existing optical microprobes utilize exotic metamaterials with a negative index of refraction, permittivity, and permeability and are extremely challenging to fabricate. In addition, these exotic metamaterials have a limited usable frequency range. Still further existing optical microprobes utilize single transparent dielectric microspheres or microcylinders (with wavelength-scale dimensions) and generate tightly focused beams referred to as photonic nanojets that are comparable to the diffraction limit laterally and one or two wavelengths long with reasonably small losses, but these photonic nanojets may be obtained only in the case of perfect plane wave illumination. In addition, such optical microprobes require the use of single mode fibers (SMFs) or inflexible waveguides, not readily available in or suitable for many applications. A concrete example of such an application is laser-tissue surgery, which is typically performed in the mid-IR range, where SMF is currently not available. Most practical radiation sources available provide diverging multimode beams of light. In most practical applications, the use of robust and flexible waveguides, including optical fibers (i.e. multi mode fiber (MMF)) and hollow waveguides is desirable. Finally, in all of the above cases, it is difficult to control the separation between the tip of the microprobe and the sample, also referred to as the "working distance," with the accuracy required. More importantly, if the focusing of light is required in a contact mode, it is practically impossible to achieve wavelength-scale focused spot sizes in sample/tissue for microprobes operating in a far field due to the high refractive index of the sample/tissue.

Thus, what are still needed in the art are optical microprobe devices and methods that provide reasonably high spatial resolution (on the order of λ or smaller), the efficient transmission of optical power from multimodal radiation source to sample, have a readily controllable working distance with a simple setup, are capable of being operated in a contact mode, and that incorporate robust and flexible optical fiber or hollow waveguides, all without the need for "perfect" radiation sources or exotic, expensive materials.

BRIEF SUMMARY OF THE INVENTION

In various exemplary embodiments, the present invention provides optical microprobe devices and methods that utilize a plurality of transparent or semitransparent small scale spheres, cylinders, or the like of the same or varying size and the same or varying index of refraction to focus a beam of light and create a usable photonic nanojet, thereby providing reasonably high spatial resolution (i.e. on the order of or smaller than λ) and high optical throughput. In the simplest case, the small scale spheres or cylinders are axially chained together in a contact configuration within a hollow waveguide, a hollow-core photonic crystal fiber, in a capillary tube, integrated with an optical fiber, or assembled on a chip or other substrate (patterned or non-patterned), with the last small scale sphere or cylinder adjacent and/or exposed to an external medium. This periodically focuses coupled light along the chain, giving rise to periodic optical modes referred to as photonic "nanojet induced modes" (NIMs). If desired, focused beams with progressively smaller dimensions may be obtained along the chain. The last photonic nanojet is operable for acting on a specimen. Non-axial and non-contact configurations (both regular and irregular) are also contemplated. These optical microprobe devices and methods find applicability in material and biomedical modification and cutting applications (possibly in combination with conventional or novel micromanipulation techniques), such as laser-tissue surgery, material analysis applications, data storage applications, and the like. Advantageously, the optical microprobes of the present invention may utilize radiation sources with narrow spectral lines (i.e. lasers) or broad emission spectra, operate over a wide range of wavelengths and frequencies, may be used in multimodal systems with "imperfect" radiation sources, and provide the efficient coupling of radiation source to focusing element, with relatively small losses in the transmission of optical power. Further, the optical microprobes of the present invention are designed to operate over very short working distances and are not unacceptably affected by specimen contact. Still further, the optical microprobes of the present invention may be used in conjunction with robust and flexible multimodal optical fiber or hollow waveguides. In addition, the optical microprobes of the present invention may operate as sealed devices, making them more impervious to environmental intrusion. Finally, the microspheres or microcylinders in the microprobes of the present invention may be made of optically nonlinear or optically active materials. This allows using the above-described light-focusing effects in combination with such effects as nonlinear frequency generation, optical amplification, and lasing. In these applications, the periodicity of the chain provides a quazi-phase-matching condition for nonlinear frequency generation or optical feedback for lasing. Due to the high concentration of light in the photonic nanojet regions inside the spheres or cylinders, such structures have increased nonlinear response and reduced lasing threshold combined with tight focusing of the output beams, a highly desirable combination of properties in many optoelectonic applications.

Exemplary applications of the optical microprobe devices of the present invention include a compact focusing device for the coupling of light into photonic structures for the patterning of materials with submicron resolution, as a laser scalpel for minimally invasive tissue modification, as an ultracompact device on a chip for forming tiny holes in thin films or the patterning of materials, as a spectroscopic analysis tool for the compositional analysis of nanoparticles and surface contaminants, etc. Exemplary applications of the optical microprobe devices of the present invention also include for frequency harmonic or laser generation under conditions of tight focusing of the output beams.

In one exemplary embodiment, the present invention provides an optical microprobe device for focusing multimodal radiation with wavelength-scale spatial resolution and delivering the focused radiation to a specimen, including: a radiation source; and one or more of a plurality of optically transparent or semitransparent spheres and a plurality of optically transparent or semitransparent cylinders optically coupled to the radiation source; wherein the one or more of the plurality of optically transparent or semitransparent spheres and the plurality of optically transparent or semitransparent cylinders periodically focus radiation optically transmitted from the radiation source such that radiation ultimately transmitted to the specimen has predetermined characteristics. Preferably, the radiation ultimately transmitted to the specimen has a critical size on the order of or less than a wavelength of the radiation. Optionally, all of the spheres or cylinders have the same size. Optionally, the spheres or cylinders have varying sizes. Optionally, all of the spheres or cylinders have the same index of refraction. Optionally, the spheres or cylinders have varying indices of refraction. Optionally, the spheres or cylinders are aligned along a primary axis. Optionally, the spheres or cylinders are in direct physical contact. Preferably, the spheres or cylinders are assembled inside one of a hollow waveguide, a hollow-core photonic crystal fiber, a capillary tube, and integrated in a multimode fiber. Optionally, the structure is infiltrated with a liquid material with the ability to solidify to provide structural integrity and protection from external factors. Alternatively, the spheres or cylinders are assembled on a substrate. Optionally, the optical microprobe device also includes one or more of a waveguide, an optical fiber, a lens, and an optical structure disposed between the radiation source and the spheres or cylinders. Optionally, the microspheres or cylinders are made of optically nonlinear or active materials.

In another exemplary embodiment, the present invention provides an optical microprobe method for focusing multimodal radiation with wavelength-scale spatial resolution and delivering the focused radiation to a specimen, including: providing a radiation source; and providing one or more of a plurality of optically transparent or semitransparent spheres and a plurality of optically transparent or semitransparent cylinders optically coupled to the radiation source; wherein the one or more of the plurality of optically transparent or semitransparent spheres and the plurality of optically transparent or semitransparent cylinders periodically focus radiation optically transmitted from the radiation source such that radiation ultimately transmitted to the specimen has predetermined characteristics. Preferably, the radiation ultimately transmitted to the specimen has a critical size on the order of or less than a wavelength of the radiation. Optionally, all of the spheres or cylinders have the same size. Optionally, the spheres or cylinders have varying sizes. Optionally, all of the spheres or cylinders have the same index of refraction. Optionally, the spheres or cylinders have varying indices of refraction. Optionally, the spheres or cylinders are aligned along a primary axis. Optionally, the spheres or cylinders are in direct physical contact. Preferably, the spheres or cylinders are assembled inside one of a hollow waveguide, a hollow-core photonic crystal fiber, a capillary tube, and integrated in a multimode fiber. Optionally, the structure is infiltrated with a liquid material with the ability to solidify to provide structural integrity and protection from external factors. Alternatively, the spheres or cylinders are assembled on a substrate. Optionally, the optical microprobe method also includes providing one or more of a waveguide, an optical fiber, a lens, and an optical structure disposed between the radiation source and the spheres or cylinders. Optionally, the microspheres or cylinders are made of optically nonlinear or active materials.

In a further exemplary embodiments, the present invention provides an optical microprobe device for focusing multimodal radiation with wavelength-scale spatial resolution and delivering the focused radiation to a specimen, including: a radiation source; and one or more of a plurality of optically transparent or semitransparent spheres and a plurality of optically transparent or semitransparent cylinders optically coupled to the radiation source; wherein the one or more of the plurality of optically transparent or semitransparent spheres and the plurality of optically transparent or semitransparent cylinders periodically focus radiation optically transmitted from the radiation source creating periodic focused beams such that radiation ultimately transmitted to the specimen forms a final focused beam that has predetermined characteristics.

BRIEF DESCRIPTION OF THE DRAWINGS

The present invention is illustrated and described herein with reference to the various drawings, in which like reference numbers are used to denote like device components/method steps, as appropriate, and in which:

FIG. 4 is a schematic diagram illustrating another exemplary embodiment of the focusing multimodal microprobe device of the present invention used as a focusing tool, the focusing multimodal microprobe device including a radiation source optically coupled via a conventional lens to a plurality of transparent or semitransparent small scale spheres, cylinders, or the like disposed within or forming a part of a hollow waveguide, a hollow-core photonic crystal fiber, a capillary tube, integrated in a multimode fiber, or the like;

DETAILED DESCRIPTION OF THE INVENTION

In accordance with the devices and methods of the present invention, the teem "optical microprobe" is defined as an instrument that is capable of selectively applying a stable and focused beam of light or other radiation to a small scale portion of a sample in a directed manner for modification, analytical, or other purposes. It is variously also referred to herein as a "focusing multimodal microprobe." These and all similar terms should be considered to be synonomous.

Figure 1:
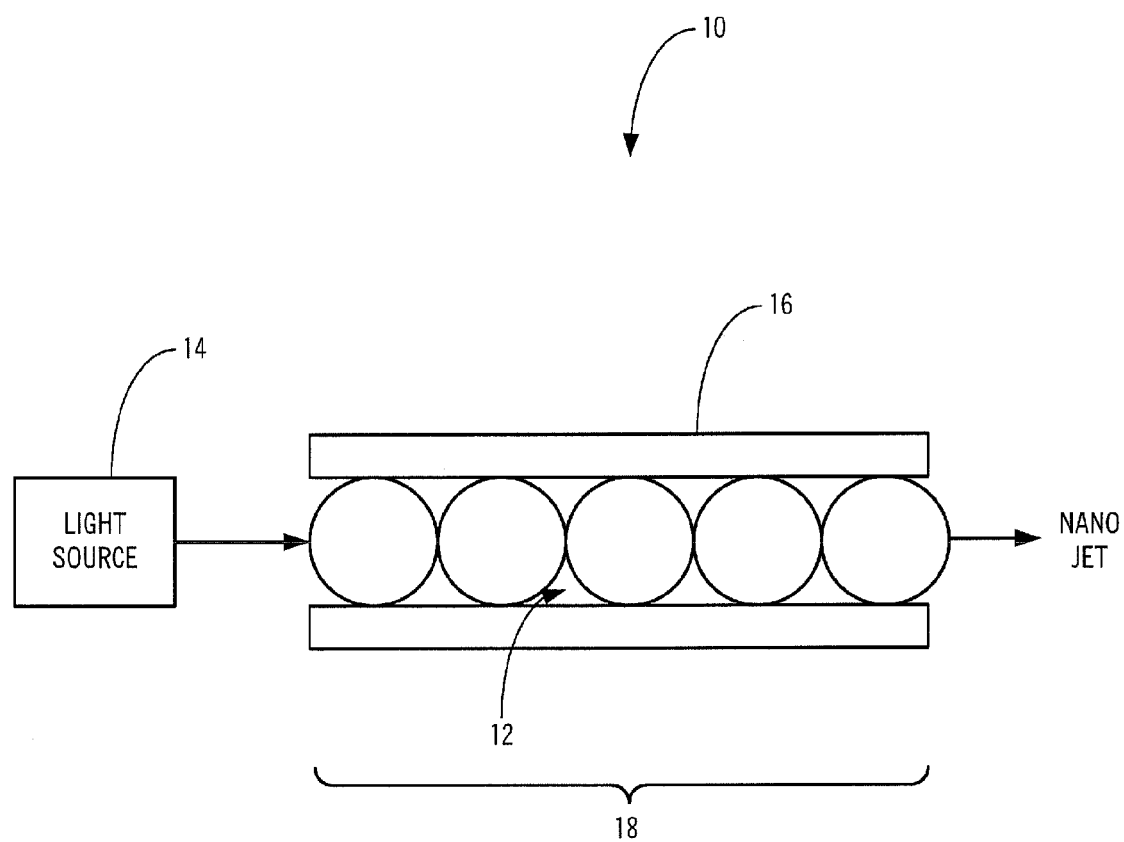
FIG. 1 is a schematic diagram illustrating one exemplary embodiment of the focusing multimodal microprobe device of the present invention, the optical microprobe device including a radiation source optically coupled to a plurality of transparent or semitransparent small scale spheres, cylinders, or the like disposed within or forming a part of a hollow waveguide, a hollow-core photonic crystal fiber, a capillary tube, integrated in a multimode fiber, or the like, or disposed on a substrate.

Referring to FIG. 1, in one exemplary embodiment of the optical microprobe 10 of the present invention, a plurality of transparent or semitransparent small scale spheres, cylinders, or the like 12 of the same or varying size and the same or varying index of refraction are used to focus a beam of light or other radiation selectively emitted by an optically coupled radiation source 14. Preferably, these spheres or cylinders 12 each have a diameter of between about one wavelength of light and several thousand wavelengths of light, and are made of a dielectric or semiconductor material or the like that is at least partially transparent in a given spectral range. Optionally, an odd number of spheres or cylinders 12 between about 3 and about 7 are used. The radiation source 14 may be, for example, a laser, a light-emitting diode, a fiber-integrated source, a white-light source, sunlight, etc. It should be noted that many others shapes may also find applicability to the inventive concepts of the present invention, provided that they suitably focus a beam of light or other radiation and create a usable photonic nanonjet, thereby ultimately providing the optical microprobe 10 of the present invention with wavelength-scale spatial resolution combined with high optical throughput.

In the simple embodiment illustrated, the spheres or cylinders 12 are axially chained together in a contact configuration within an at least axially radiation transmissive housing 16, such as a hollow waveguide, a hollow-core photonic crystal fiber, or optical fiber (i.e. the spheres or cylinders 12 may be infiltrated into the core of a hollow waveguide or integrated with an optical fiber), in a capillary tube, or on a chip or other substrate (patterned or non-patterned). This housing 16 may be, for example, a 300-micron diameter cylindrical hollow waveguide with sidewalls coated with a thin layer of light-reflecting metal, a glass microcapillary tube with semitransparent sidewalls, etc., although other suitable configurations, materials, and/or dimensions may be utilized. Preferably, at least one of the spheres or cylinders 12 is adjacent and/or exposed to an external medium through or adjacent to the housing 16 and, optionally, the last sphere or cylinder 12 is adjacent and/or exposed to the external medium through or adjacent to the housing 16. This configuration periodically focuses coupled light along the chain, giving rise to periodic NIMs. If desired, focused beams with progressively smaller dimensions may be obtained along the chain. The exposed or last photonic nanojet is operable for acting on a specimen.

Non-axial and non-contact configurations (both regular and irregular) are also contemplated, with the spheres or cylinders 12 arranged in a variety of patterns either touching or not touching one another. For example, a plurality of bunched optical fibers, rods, capillaries, or other cylindrical elements could be attached to a substrate. All of these optical microprobe devices 10 find applicability in material and biomedical modification and cutting applications, material analysis applications, data storage applications, and the like. Advantageously, the optical microprobes 10 of the present invention may utilize radiation sources 14 with narrow spectral lines (i.e. lasers) or broad emission spectra, operate over a wide range of wavelengths and frequencies, may be used in multimodal systems with "imperfect" radiation sources 14, and provide the efficient coupling of radiation source 14 to focusing element 18, with relatively small losses in the transmission of optical power. Further, the optical microprobes 10 of the present invention are designed to operate over very short working distances, on the order of between about 0 microns and several millimeters, and are not unacceptably affected by specimen contact. Still further, the optical microprobes of the present invention may be used in conjunction with robust and flexible multimodal optical fiber or hollow waveguides.

Figure 2:
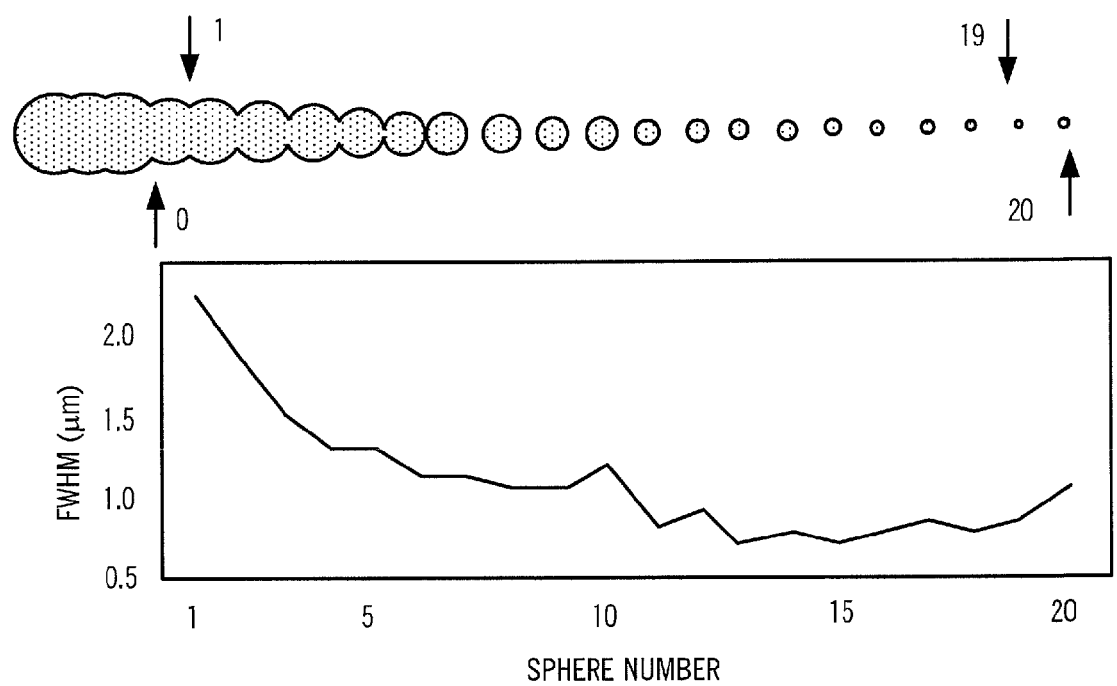
FIG. 2 is a scattering image illustrating the propagation of light away from a fluorescent source through an axial chain of spheres or cylinders and a plot illustrating the narrowing of the associated photonic nanojets down to wavelength-scale sizes along the axial chain.

Referring to FIG. 2, as alluded to above, the periodic focusing of beams of light emitted by a fluorescent source by spherical or cylindrical microlenses leads to the formation of periodically focused beams of light inside the chain. The quasi-periodic optical modes obtained are the NIMs. In the case of spherical microlenses, the focused beams of light are constrained in all three spatial dimensions. Whereas, in the case of cylindrical microlenses, the focused beams of light are constrained in the two dimensions perpendicular to the axis of the cylinders and extend along the axis of the cylinders. Periodically focused beams may have different locations inside such chains of spherical or cylindrical microlenses, depending on their size, index of refraction, and separation. It has been experimentally demonstrated that for 2-10 μm spheres or cylinders 12 (FIG. 1) with an index of refraction of 1.59, the focused beams of light are located close to the contact point(s) between the spheres or cylinders 12, as illustrated in FIG. 2b.

Figure 3:
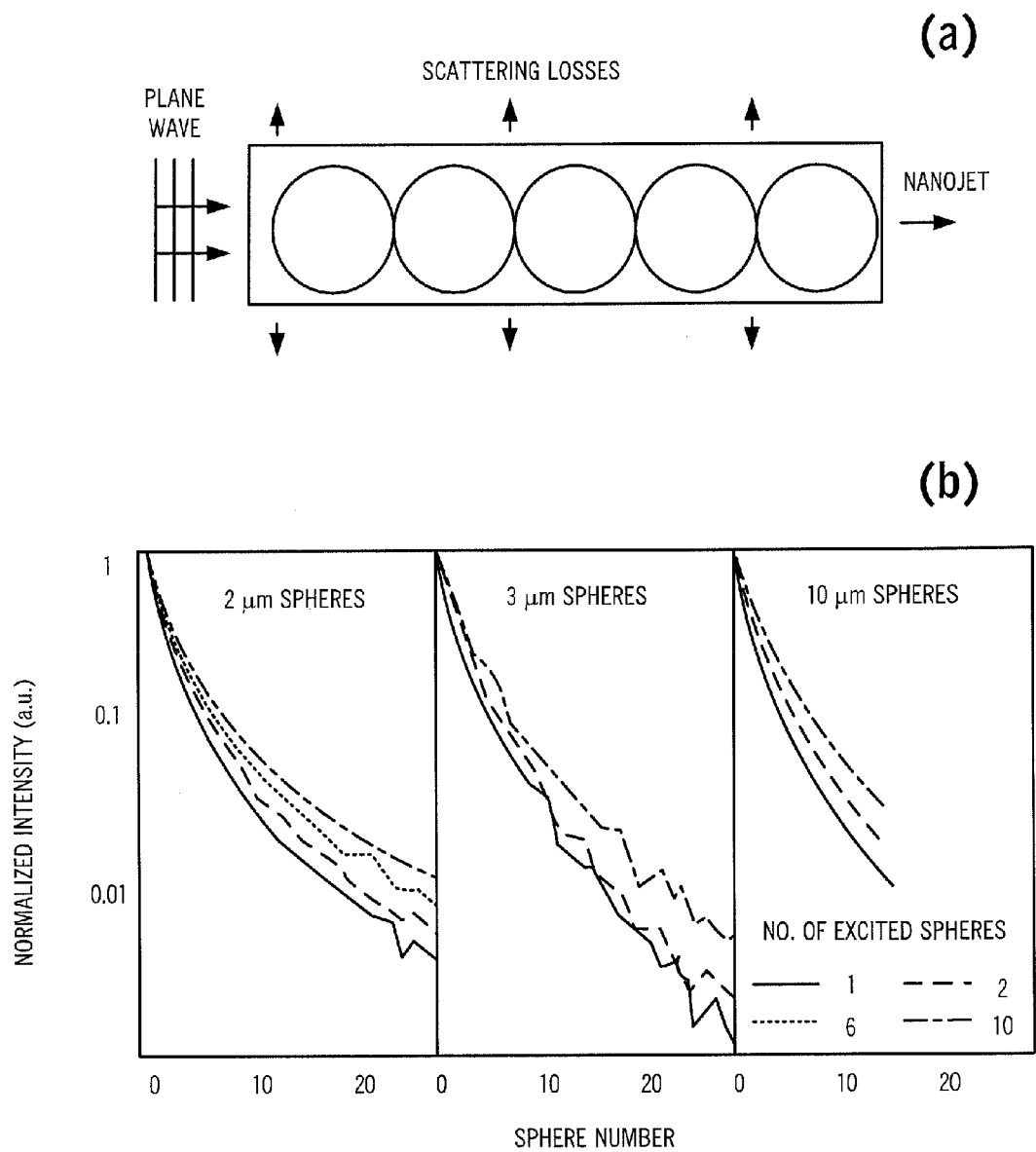
FIGS. 3a and 3b are a conceptual diagram illustrating calculated periodic focusing of a beam of light in 5 μm spheres or cylinders arranged in an axial chain and a series of plots illustrating the intensity of the associated periodic focused beams measured along the axial chain for spheres or cylinders of different sizes.

The present invention uses a gradual "tapering" of the focused beams of light observed in such axial chains (see the full width at half maximum (FWHM) data presented in FIG. 2b). Due to the multimodal nature of the radiation source 14 (FIG. 1) used in these experiments, the focused beams of light have relatively large sizes in the first few spheres or cylinders 12 adjacent to the radiation source 14. However, in more distant spheres or cylinders 12, the sizes of the focused beams of light are found to be significantly diminished. This effect occurs due to the progressive filtering of the paraxial modes with the smallest propagation losses. Based on numerical finite differential time domain (FDTD) modeling, it may be suggested that these modes have a period roughly equal to the size of two of the touching spheres or cylinders 12, as illustrated in FIG. 3a. These NIMs dominate the transmission properties of long chains of spheres or cylinders 12 with attenuation approaching ~0.1 dB/sphere or cylinder. They are also characterized with the smallest wavelength-scale sizes of the focused beams of light. The physical explanation of the small propagation losses for NIMs is connected with the fact that beams propagating in the vicinity of the contact point between the spheres or cylinders experience almost no reflection if the separation between the two spherical or cylindrical interfaces is smaller than the wavelength of light in a near-contact area of touching spheres or cylinders. In addition, the optical losses and mode filtering properties of such structures may be controlled by creating "micro-joints" around the contact points of spheres or cylinders. Such micro joints develop naturally between polystyrene structures, for example, due to the partial dissolving of the structures in an aqueous environment, also referred to as a "swelling" effect. These micro-joints may be controlled by chemical means using various surfactants added to the solution surrounding the structures. Under these conditions, light may optically tunnel from sphere to sphere or cylinder to cylinder with minimal propagation losses. Thus, sources of light 14 with broad directionality of emission may be coupled to NIMs in such axial chains. The coupling losses in the first ten (10) spheres or cylinders 12 required for achieving wavelength-scale beam sizes are on the order of 10-20 dB, as illustrated in FIG. 3b. This result was obtained using fluorescent dye-doped microspheres with very broad directionality of emission as a source of light. By using radiation sources 14 with more collimated beams, such as optical fibers or hollow waveguides, the coupling losses may be further reduced. In chains formed by 3-7 spheres, for example, the total transmitted power is expected to be larger than 0.1. The transmission coefficient may be further optimized in hollow waveguide structures, where scattered photons may be recycled for focusing applications due to reflections provided by the metalized sidewalls, for example. Thus, optical microprobe device 10 (FIG. 1) of the present invention possesses significantly higher optical throughput capability as compared to conventional near field optical microprobes.

In addition, the exposed or last photonic nanojet in such axial chains appears in close proximity to the surface of the end sphere or cylinder 12 in the axial chain, allowing the use of the optical microprobe 10 in a contact mode with the specimen or tissue under modification or examination. The focusing properties of such axial chains of spheres or cylinders 12 are perturbed by the external medium to a significantly lesser extent as compared to conventional microprobes, as the focusing is accomplished primarily inside the axial chain. Optionally, the exposed end sphere or cylinder 12 in the axial chain is made from a material with a higher index of refraction as compared to the other spheres or cylinders 12 in order to provide focusing in a specimen in a close proximity to the surface of the end sphere or cylinder 12.

Figure 4:
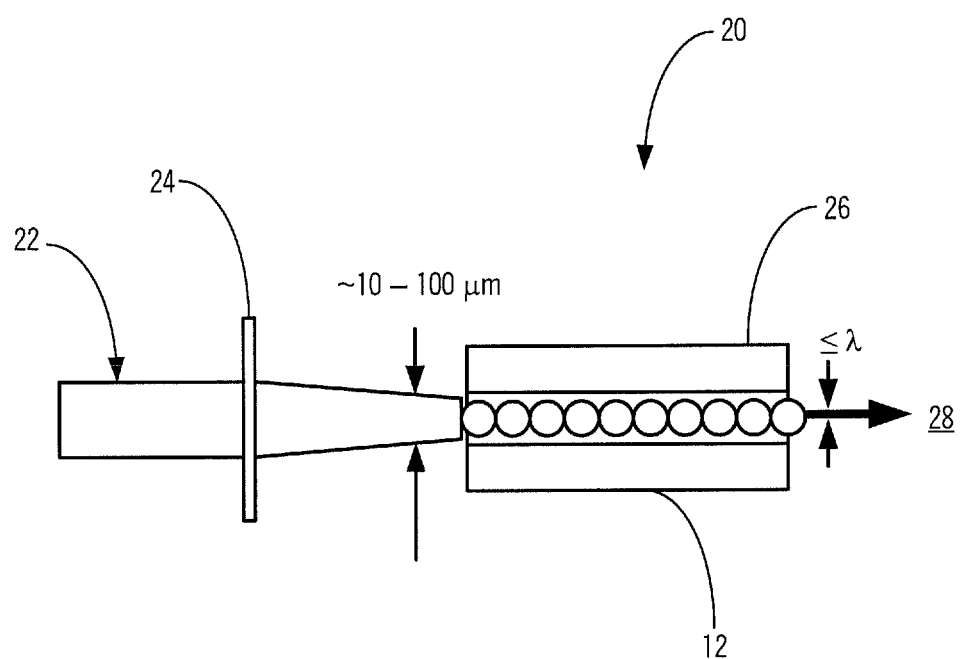

Referring to FIG. 4, in another exemplary embodiment of the optical microprobe 20 of the present invention, a multimodal incident beam of light 22 is focused by a conventional lens 24 down to ~10-100 µm size. This beam of light 22 is then coupled to NIMs in an axial chain of spheres or cylinders 12 assembled inside a hollow waveguide or capillary tube 26. The last nanojet 28 with the wavelength scale or subwavelength scale dimensions is then exposed to a specimen. The conventional lens 24 may be replaced with any device for creating a narrow beam of light, such as a laser, a tapered optical fiber, or the like. Although only one incident beam of light 22 is illustrated in FIG. 4, more than one beam of light 22 may be used for the simultaneous focusing of light at different wavelengths on the same sample area. The number of the spheres or cylinders 12 in the axial chain may be optimized according to a trade off between the spot sizes and optical losses. Longer axial chains provide smaller spot sizes, but the optical losses are higher.

Figure 5A:
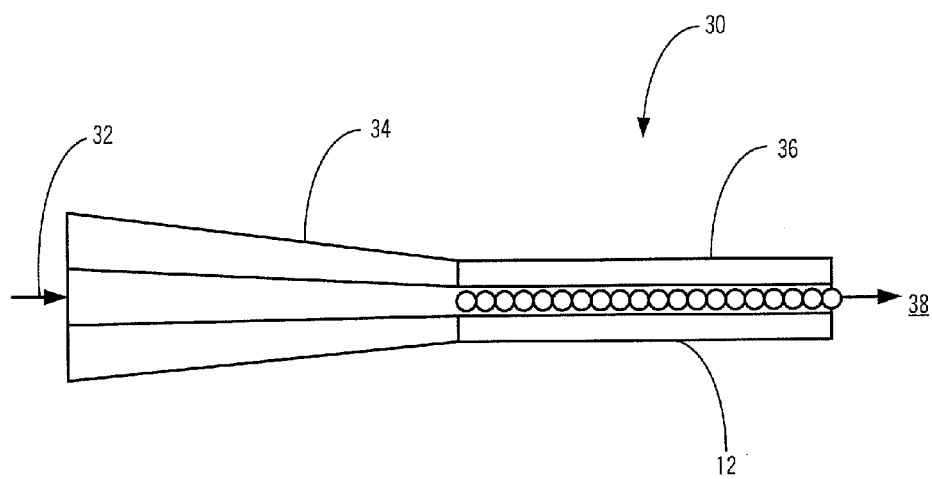
FIGS. 5a and 5b are schematic diagrams illustrating a further exemplary embodiment of the focusing multimodal microprobe device of the present invention used as an "optical scalpel" tool, the optical microprobe device including a radiation source optically coupled via a flexible optical transmission structure to a plurality of transparent or semitransparent small scale spheres, cylinders, or the like disposed within or forming a part of a hollow waveguide, a hollow-core photonic crystal fiber, a capillary tube, or the like (integration of the focusing multimodal microprobe device with a multimode fiber is illustrated in FIG. 5b, with the fiber inserted in a capillary tube or the like and the volume inside the capillary tube infiltrated with an optically transparent liquid material with the ability to solidify—providing structural integrity and protection from external factors; the liquid core of the structure designed to operate as a waveguide to reduce optical losses)
Figure 5B:
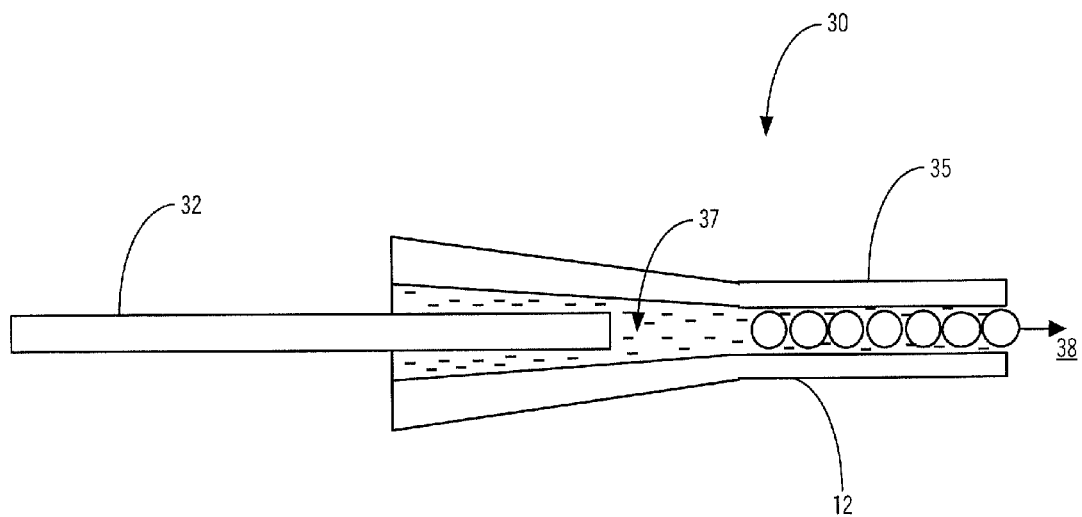

Referring to FIG. 5, in a further exemplary embodiment of the optical microprobe 30 of the present invention, the incident beam of light 32 from a medical laser 34 or the like is coupled to NIMs in an axial chain of spheres or cylinders 12 assembled inside a hollow waveguide 36. The last nanojet 38 with the wavelength scale or subwavelength scale dimensions is then used for ultraprecise surgery, for example, or another cutting or surface modification application. It will be readily apparent to those of ordinary skill in the art that the hollow waveguide 36 represents only one of the numerous possible realizations of an "optical scalpel." The advantage of this design is that the spheres or cylinders 12 may be integrated inside the hollow waveguide delivery system of a standard mid-infrared medical laser, such as an Erbium:YSGG laser at 2.79 µm or an Erbium:YAG laser at 2.94 µm. However, it will be readily apparent to those of ordinary skill in the art that the light delivered by any flexible waveguide delivery system may be coupled to an axial chain or other arrangement of spheres or cylinders 12 using additional focusing elements, such as lenses, etc. In this case, the axial chain of spheres or cylinders 12 is preferably mechanically and optically integrated into and with the delivery system. An example of such integration with multimodal fiber is illustrated in FIG. 5b. The fiber 33 is inserted in a capillary tube 35 or the like. The volume inside the capillary tube 35 is infiltrated with an optically-transparent or semitransparent liquid material 37 with the ability to solidify to provide structural integrity and protection from external factors. In addition, the liquid core of the structure is designed to operate as a waveguide to reduce optical losses. The refractive index of spheres or cylinders may be much higher than the index of the liquid core, so that the effects of periodical focusing take place inside such a core leading to the formation of small, wavelength-scale nanojet 38. As an example, a liquid core with refractive index 1.56 may be used in combination with barium-titanate glass microspheres or microcylinders with refractive index 2.1.

Figure 6:
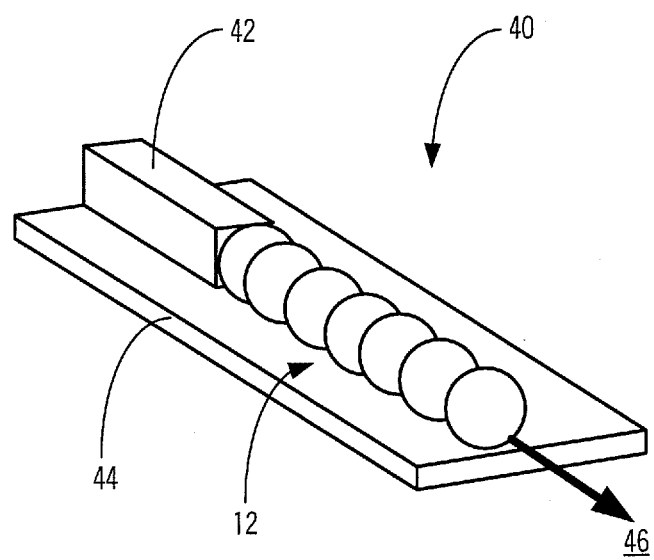
FIG. 6 is a schematic diagram illustrating a still further exemplary embodiment of the focusing multimodal microprobe device of the present invention representing a chip scale local surface modification tool, the focusing multimodal microprobe device including a radiation source optically coupled to a plurality of transparent or semitransparent small scale spheres or the like disposed on a substrate.
Figure 7:
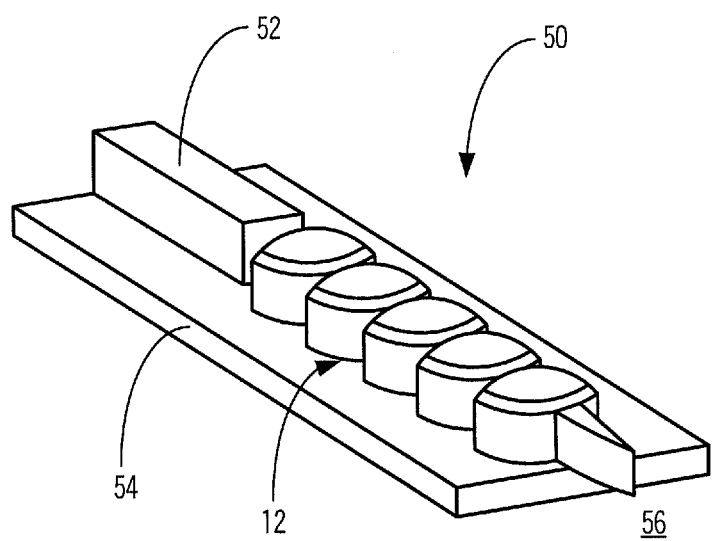
FIG. 7 is a schematic diagram illustrating a still further exemplary embodiment of the focusing multimodal microprobe device of the present invention representing a chip scale stripe surface modification tool, the focusing multimodal microprobe device including a radiation source optically coupled to a plurality of transparent or semitransparent small scale cylinders or the like disposed on a substrate.

FIG. 6 is a schematic diagram illustrating a still further exemplary embodiment of the optical microprobe device 40 of the present invention representing a chip scale point surface modification tool, the optical microprobe device 40 including a radiation source 42 optically coupled to a plurality of transparent or semitransparent small scale spheres or the like 12 disposed on a substrate 44. Likewise, FIG. 7 is a schematic diagram illustrating a still further exemplary embodiment of the optical microprobe device 50 of the present invention representing a chip scale line surface modification tool, the optical microprobe device 50 including a radiation source 52 optically coupled to a plurality of transparent or semitransparent small scale cylinders or the like 12 disposed on a substrate 54. These optical microprobe devices 40, 50 may be used as chip scale light sources for making tiny holes in thin films or for the patterning of the surfaces of various materials, for example. The radiation sources 42, 52, such as light emitting diodes or semiconductor lasers, are grown or heterogeneously integrated on the substrate 44, 54. Due to the mode filtering in the axial chain of microspheres 12, the last photonic nanojet 46 is three dimensionally confined in close proximity to the end sphere 12 in the chain. In contrast, as schematically illustrated in FIG. 7, due to the mode filtering in the axial chain of microcylinders 12, a narrow "strip" of light 56 extends along the axis of the cylinders 12. This may be used in specific applications requiring illumination with a narrow distribution of light intensity extending in one direction. As alluded to above, the cylinders 12 in the optical system 50 may be formed by bunched fibers, capillaries, or any elements with cylindrical symmetry, such as, for example, micropillars fabricated on the same chip as a semiconductor laser. Moreover, while the optical systems 40, 50 are illustrated using integration on the same substrate, it will be readily apparent to those of ordinary skill in the art that such spherical or cylindrical elements may be heterogeneously integrated with the external sources of light without using a common substrate.

Figure 8:
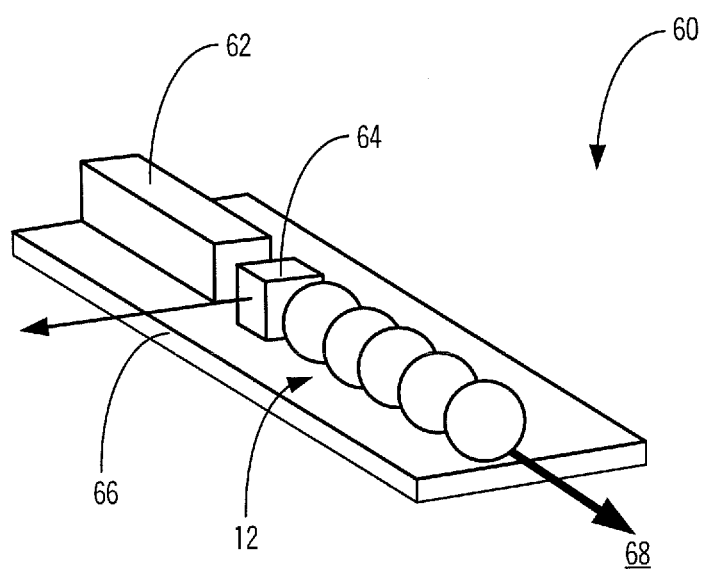
FIG. 8 is a schematic diagram illustrating a still further exemplary embodiment of the focusing multimodal microprobe device of the present invention representing a spectral analysis tool, the focusing multimodal microprobe device including a radiation source optically coupled through a semitransparent/partially reflective structure to a plurality of transparent or semitransparent small scale spheres, cylinders, or the like disposed on a substrate.

FIG. 8 is a schematic diagram illustrating a still further exemplary embodiment of the optical microprobe device 60 of the present invention representing a spectral analysis tool, the optical microprobe device 60 including a radiation source 62 optically coupled through a semitransparent/partially reflective structure 64 to a plurality of transparent or semitransparent small scale spheres, cylinders, or the like 12 disposed on a substrate 66. The radiation source 62, such as a light emitting diode or semiconductor laser, is grown or heterogeneously integrated on the substrate 66. Due to the mode filtering in the axial chain of microspheres or microcylinders 12, the last photonic nanojet 68 is two or three dimensionally confined in close proximity to the end sphere 12. This photonic nanojet 68 is selectively exposed to small particles, cells, or various surface contaminants under examination. The light reflected, scattered, or emitted by these particles is collected by the same axial chain of spheres or cylinders 12 and reflected by the semitransparent/partially reflective structure 64 into a photodiode and/or spectrum analyzing system (not illustrated).

Figure 9:
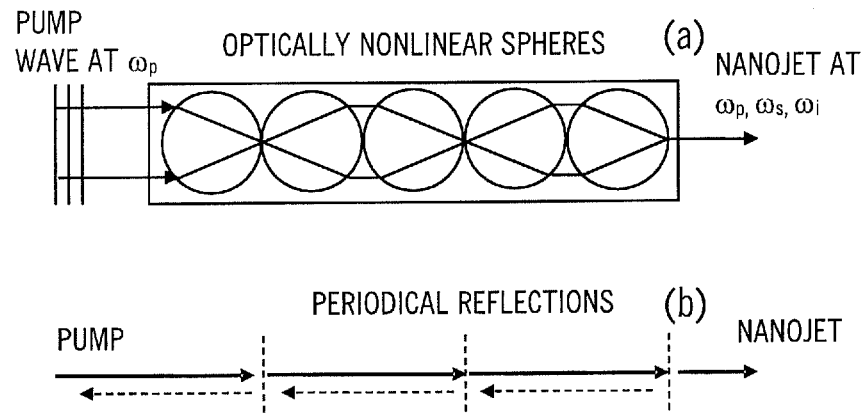
FIGS. 9a and 9b are conceptual diagrams illustrating a still further exemplary embodiment of the focusing multimodal microprobe device of the present invention representing an optical parametric oscillator, the focusing multimodal microprobe device including a pump source at frequency $\omega_p$ optically coupled through a semitransparent/partially reflective structure to a plurality of transparent or semitransparent small scale spheres or cylinders made from optically nonlinear material and deposited within or forming a part of a hollow waveguide, a hollow-core photonic crystal fiber, or integrated with an optical fiber, or the like—the quazi-phase-matching condition is provided due to spatially periodic reflections in the chain, as schematically illustrated in FIG. 9b.

FIGS. 9a and 9b are conceptual diagrams illustrating a still further exemplary embodiment of the focusing multimodal microprobe device of the present invention representing an optical parametric oscillator, the focusing multimodal microprobe device including a pump source at frequency $\omega_p$ optically coupled through a semitransparent/partially reflective structure to a plurality of transparent or semitransparent small scale spheres or cylinders made from optically nonlinear material and deposited within or forming a part of a hollow waveguide, a hollow-core photonic crystal fiber, or integrated with an optical fiber, or the like. The quazi-phase-matching condition is provided due to spatially periodic reflections in the chain, as schematically illustrated in FIG. 9b. As a possibility, the microspheres or microcylinders may be fabricated from high refractive index barium-titanate glass and covered with metallic nanoparticles, organic molecules, or quantum dots or wires to enhance third-order nonlinear susceptibility. As a possibility, a single-frequency ($\omega_p$) laser source may be used as a pump. Due to second order nonlinear interaction, the microprobe is expected to generate light at two frequencies called signal ($\omega_s$) and idler ($\omega_i$), so that the condition $\omega_s+\omega_i=\omega_p$ is preserved. The frequency generation process is expected to occur in the areas of highest pump intensities represented by photonic nanojets inside the chain. Due to high pump power density in these areas the threshold for nonlinear frequency generation is expected to be greatly reduced in such microprobes. Due to spatial overlap of the pump, signal and idler beams all three beams at frequencies $\omega_p$, $\omega_s$, and $\omega_i$ maybe be tightly focused by the microprobe.

Figure 10:
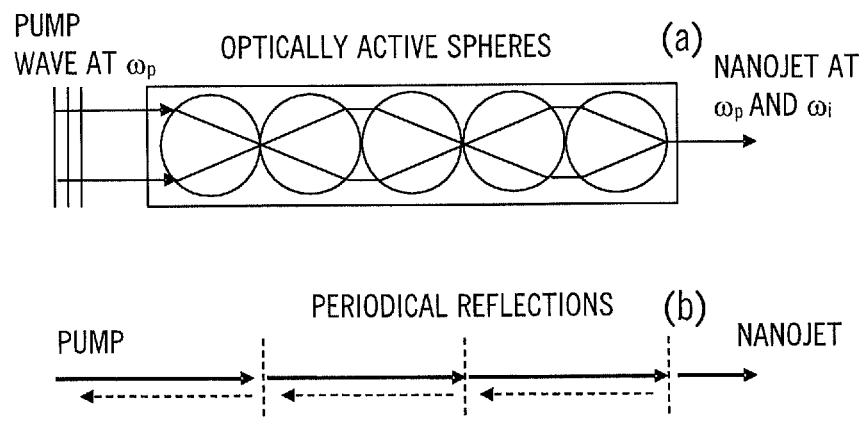
FIGS. 10a and 10b are conceptual diagrams illustrating a still further exemplary embodiment of the focusing multimodal microprobe device of the present invention representing a laser, the focusing multimodal microprobe device including a pump source at frequency $\omega_p$ optically coupled through a semitransparent/partially reflective structure to a plurality of transparent or semitransparent small scale spheres or cylinders made from optically active material and deposited within or forming a part of a hollow waveguide, a hollow-core photonic crystal fiber, or integrated with an optical fiber, or the like—the optical feedback is provided due to spatially periodic reflections in the chain, as schematically illustrated in FIG. 10b.

FIGS. 10a and 10b are conceptual diagrams illustrating a still further exemplary embodiment of the focusing multimodal microprobe device of the present invention representing a laser, the focusing multimodal microprobe device including a pump source at frequency $\omega_p$ optically coupled through a semitransparent/partially reflective structure to a plurality of transparent or semitransparent small scale spheres or cylinders made from optically active material and deposited within or forming a part of a hollow waveguide, a hollow-core photonic crystal fiber, or integrated with an optical fiber, or the like. The optical feedback is provided due to spatially periodic reflections in the chain, as schematically illustrated in FIG. 10b. As a possibility, the microspheres or microcylinders may be fabricated from polystyrene doped with active dye molecules or from glass materials doped with active erbium ions. In the case of weak optical feedback, the microprobe may operate as an optical amplifier due to the presence of active ions or molecules. With sufficiently strong optical feedback, the microprobe may provide a laser action at the frequency $\omega_i$. The maximal optical gain is expected to occur in the areas of highest pump intensities represented by photonic nanojets inside the chain. Due to high pump power density in these areas the threshold for lasing is expected to be greatly reduced in such microprobes.

Again, in various exemplary embodiments, the present invention provides optical microprobe devices and methods that utilize a plurality of transparent or semitransparent small scale spheres, cylinders, or the like of the same or varying size and the same or varying index of refraction to focus a beam of light and create a usable photonic nanojet, thereby providing wavelength-scale spatial resolution (i.e. comparable to or smaller than $\lambda$) and high optical throughput. In the simplest case, the small scale spheres or cylinders are axially chained together in a contact configuration within a hollow waveguide, a hollow-core photonic crystal fiber, in a capillary tube, or integrated with an optical fiber, or assembled on a chip or other substrate (patterned or non-patterned), with the last small scale sphere or cylinder adjacent and/or exposed to an external medium. This periodically focuses coupled light along the chain, giving rise to periodic NIMs. If desired, photonic nanojets with progressively smaller dimensions may be obtained along the chain. The last photonic nanojet is operable for acting on a specimen. Non-axial and non-contact configurations (both regular and irregular) are also contemplated. These optical microprobe devices and methods find applicability in material and biomedical modification and cutting applications, material analysis applications, data storage applications, and the like. Advantageously, the optical microprobes of the present invention may utilize radiation sources with narrow spectral lines (i.e. lasers) or broad emission spectra, operate over a wide range of wavelengths and frequencies, may be used in multimodal systems with "imperfect" radiation sources, and provide the efficient coupling of radiation source to focusing element, with relatively small losses in the transmission of optical power. Further, the optical microprobes of the present invention are designed to operate over very short working distances and are not unacceptably affected by specimen contact. Still further, the optical microprobes of the present invention may be used in conjunction with robust and flexible optical fiber or hollow waveguides. Finally, the microspheres or microcylinders in the microprobes may be made of optically nonlinear or active materials. This allows using the above-described light focusing effects in combination with such effects as nonlinear frequency generation, optical amplification, and lasing. In these applications, the periodicity of the chain provides a quazi-phase-matching condition for nonlinear frequency generation or an optical feedback for lasing. Due to high pump power density in the nanojet areas, such microprobes should have increased nonlinear response and reduced lasing threshold combined with the tight focusing of the output beams, a highly desirable combination of properties in many optoelectonic applications.

Although the present invention has been illustrated and described herein with reference to preferred embodiments and specific examples thereof, it will be readily apparent to those of ordinary skill in the art that other embodiments and examples may perform similar functions and/or achieve like results. All such equivalent embodiments and examples are within the spirit and scope of the present invention, are contemplated thereby, and are intended to be covered by the following claims.

What is claimed is:

1. An optical microprobe device for focusing multimodal radiation with wavelength-scale spatial resolution and delivering the focused radiation to a specimen, comprising:
   a radiation source; and
   one or more of a plurality of optically transparent or semitransparent spheres and a plurality of optically transparent or semitransparent cylinders optically coupled to the radiation source;
   wherein the one or more of the plurality of optically transparent or semitransparent spheres and the plurality of optically transparent or semitransparent cylinders periodically focus radiation optically transmitted from the radiation source such that radiation ultimately transmitted to the specimen has predetermined characteristics.

2. The optical microprobe device of claim 1, wherein the radiation ultimately transmitted to the specimen has a critical size on the order of or less than a wavelength of the radiation.

3. The optical microprobe device of claim 1, wherein some or all of the spheres or cylinders are made of one or more of an optically nonlinear material and an optically active material, thereby enabling one or more of a nonlinear frequency generation application, an optical amplification application, and a lasing application.

4. The optical microprobe device of claim 1, wherein all of the spheres or cylinders have the same size.

5. The optical microprobe device of claim 1, wherein the spheres or cylinders have varying sizes.

6. The optical microprobe device of claim 1, wherein all of the spheres or cylinders have the same index of refraction.

7. The optical microprobe device of claim 1, wherein the spheres or cylinders have varying indices of refraction.

8. The optical microprobe device of claim 1, wherein the spheres or cylinders are aligned along a primary axis.

9. The optical microprobe device of claim 1, wherein the spheres or cylinders are in direct physical contact.

10. The optical microprobe device of claim 1, wherein the spheres or cylinders are assembled inside one of a hollow waveguide, a hollow-core photonic crystal fiber, a capillary tube, and integrated in a multimode fiber.

11. The optical microprobe device of claim 1, wherein the spheres or cylinders are assembled on a substrate.

12. The optical microprobe device of claim 1, further comprising one or more of a waveguide, an optical fiber, a lens, and an optical structure disposed between the radiation source and the spheres or cylinders.

13. The optical microprobe device of claim 1, further comprising a matrix material disposed about the spheres or cylinders.

14. An optical microprobe method for focusing multimodal radiation with wavelength-scale spatial resolution and delivering the focused radiation to a specimen, comprising:
providing a radiation source; and
providing one or more of a plurality of optically transparent or semitransparent spheres and a plurality of optically transparent or semitransparent cylinders optically coupled to the radiation source;
wherein the one or more of the plurality of optically transparent or semitransparent spheres and the plurality of optically transparent or semitransparent cylinders periodically focus radiation optically transmitted from the radiation source such that radiation ultimately transmitted to the specimen has predetermined characteristics.

15. The optical microprobe method of claim 14, wherein the radiation ultimately transmitted to the specimen has a critical size on the order of or less than a wavelength of the radiation.

16. The optical microprobe method of claim 14, wherein some or all of the spheres or cylinders are made of one or more of an optically nonlinear material and an optically active material, thereby enabling one or more of a nonlinear frequency generation application, an optical amplification application, and a lasing application.

17. The optical microprobe method of claim 14, wherein all of the spheres or cylinders have the same size.

18. The optical microprobe method of claim 14, wherein the spheres or cylinders have varying sizes.

19. The optical microprobe method of claim 14, wherein all of the spheres or cylinders have the same index of refraction.

20. The optical microprobe method of claim 14, wherein the spheres or cylinders have varying indices of refraction.

21. The optical microprobe method of claim 14, wherein the spheres or cylinders are aligned along a primary axis.

22. The optical microprobe method of claim 14, wherein the spheres or cylinders are in direct physical contact.

23. The optical microprobe method of claim 14, wherein the spheres or cylinders are assembled inside one of a hollow waveguide, a hollow-core photonic crystal fiber, a capillary tube, and integrated in a multimode fiber.

24. The optical microprobe method of claim 14, wherein the spheres or cylinders are assembled on a substrate.

25. The optical microprobe method of claim 14, further comprising providing one or more of a waveguide, an optical fiber, a lens, and an optical structure disposed between the radiation source and the spheres or cylinders.

26. The optical microprobe method of claim 14, further comprising providing a matrix material disposed about the spheres or cylinders.

27. An optical microprobe device for focusing multimodal radiation with wavelength-scale spatial resolution and delivering the focused radiation to a specimen, comprising:
a radiation source; and
one or more of a plurality of optically transparent or semitransparent spheres and a plurality of optically transparent or semitransparent cylinders optically coupled to the radiation source;
wherein the one or more of the plurality of optically transparent or semitransparent spheres and the plurality of optically transparent or semitransparent cylinders periodically focus radiation optically transmitted from the radiation source creating periodic focused beams such that radiation ultimately transmitted to the specimen forms a final focused beam that has predetermined characteristics.

* * * * *